United States Patent [19]

Shear et al.

[11] Patent Number: 5,503,994
[45] Date of Patent: Apr. 2, 1996

[54] SYSTEM FOR SAMPLE DETECTION WITH COMPENSATION FOR DIFFERENCE IN SENSITIVITY TO DETECTION OF COMPONENTS MOVING AT DIFFERENT VELOCITIES

[75] Inventors: Jason B. Shear, Palo Alto, Calif.; Rajeev Dadoo, Cambridge, Mass.; Harvey A. Fishman, Stanford, Calif.; Neil Shafer, Palo Alto, Calif.; Richard N. Zare, Stanford, Calif.

[73] Assignee: The Board of Trustees of the Leland Stanford Junior University, Palo Alto, Calif.

[21] Appl. No.: 134,290

[22] Filed: Oct. 8, 1993

[51] Int. Cl.$^6$ ............... G01N 21/00; G01N 21/64; G01N 35/08; C12Q 1/68
[52] U.S. Cl. ............... 436/90; 436/53; 436/86; 436/89; 436/164; 436/172; 435/6; 356/344; 204/452; 204/461
[58] Field of Search ............... 435/4, 6; 436/53, 436/164, 172, 171, 94, 86, 89, 90; 422/50, 52, 68.1, 70, 82.5, 82.08, 82.09; 356/344; 204/182.8

[56] References Cited

U.S. PATENT DOCUMENTS

| 4,729,947 | 3/1988 | Middendorf et al. | 435/6 |
| 4,769,523 | 9/1988 | Tanimoto et al. | 219/121.6 |

OTHER PUBLICATIONS

Kambara et al. (1992) Electrophoresis, vol. 13, pp. 542–546.
L. M. Smith et al., *Nature*, 321:674–679 (1986).
L. R. Middendorf et al., *Electrophoresis*, 13:487–494 (1992).
S. Pentoney et al., *Electrophoresis*, 13:467–474 (1992).
X. Huang et al., "Analysis of Facotrs Causing Peak Broadening in Capillary Zone Electrophoresis,"*Journ. of Chrom.*, 480:95–110 (1989).
J. C. White et al., "Photostability Studies of Phycobiliprotein Fluorescent Labels,"*Anal. Biochem.*, 161:442–452 (1987).

*Primary Examiner*—Mindy Fleisher
*Assistant Examiner*—Philip W. Carter
*Attorney, Agent, or Firm*—Majestic, Parsons, Siebert & Hsue

[57] ABSTRACT

In many separation techniques, such as field flow fractionation, liquid chromatography and electro-phoresis, chemical species form bands that migrate at different velocities. If the data-digitization rate and excitation intensity are both set to be optimal for the fastest migrating band, to compensate for different band velocities, both the data-digitization rate and the excitation intensity are decreased as a function of time by a factor equal to the migration time of the fastest migrating band to the separation time.

31 Claims, 6 Drawing Sheets

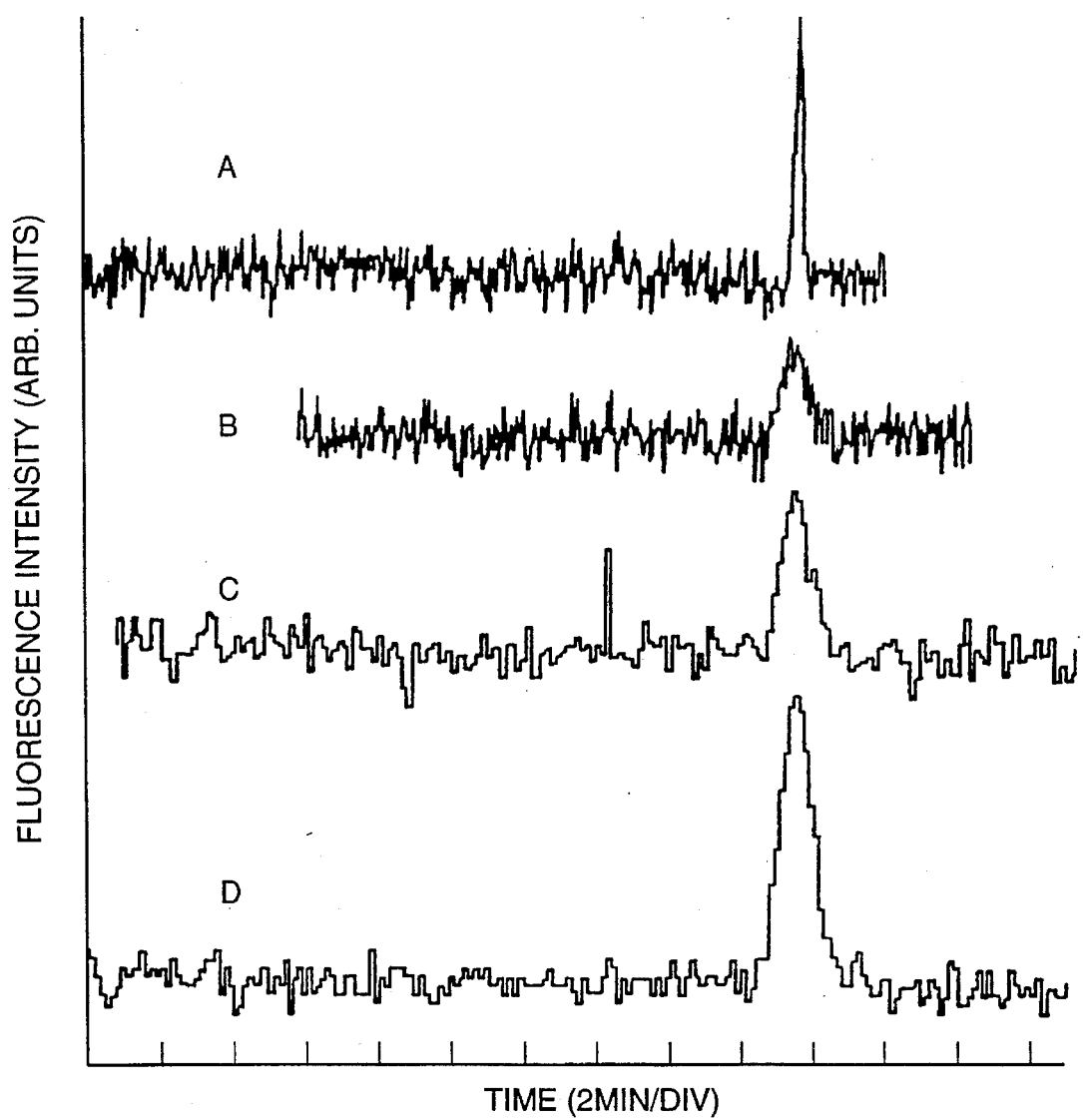
FIG._1

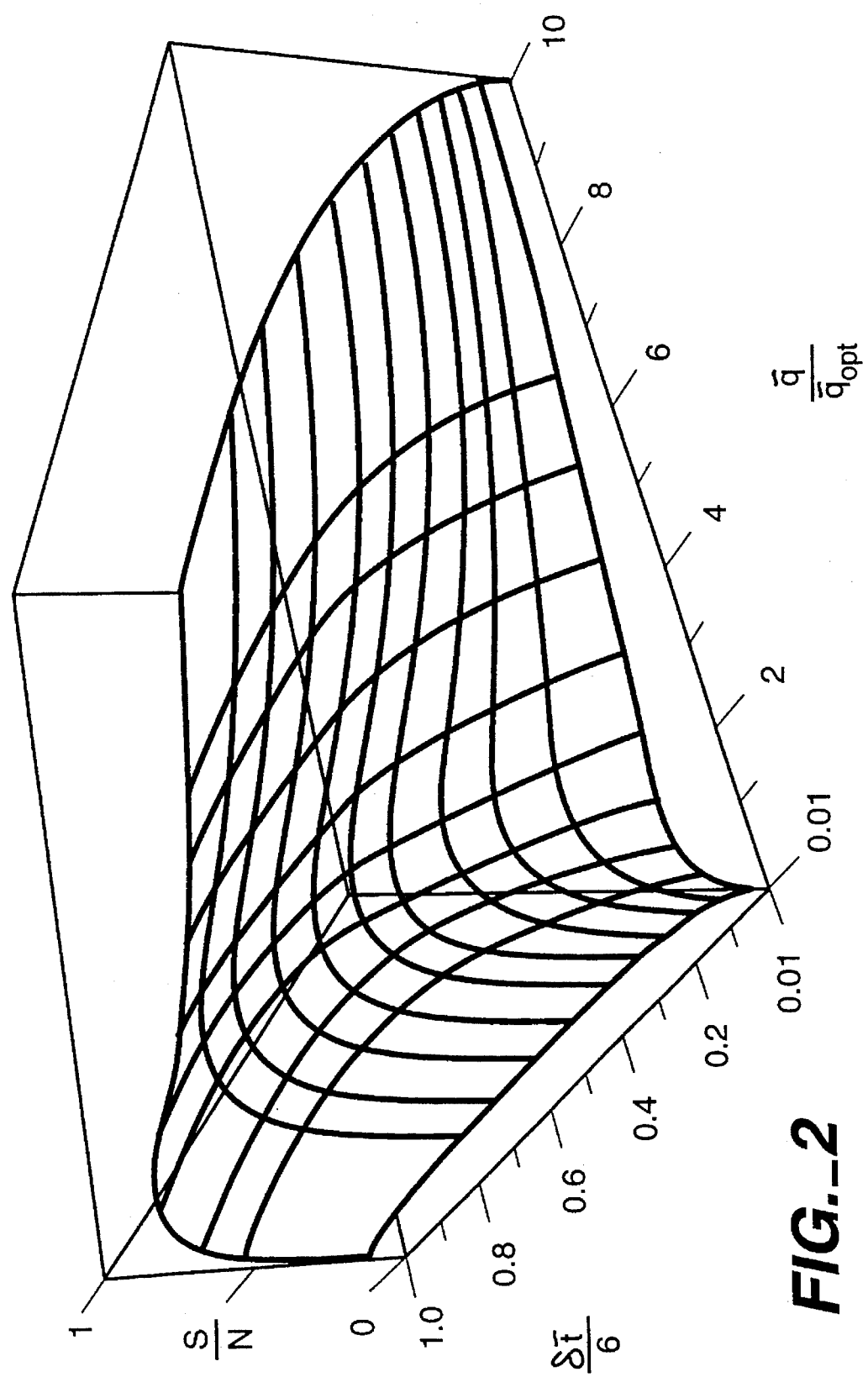
FIG._2

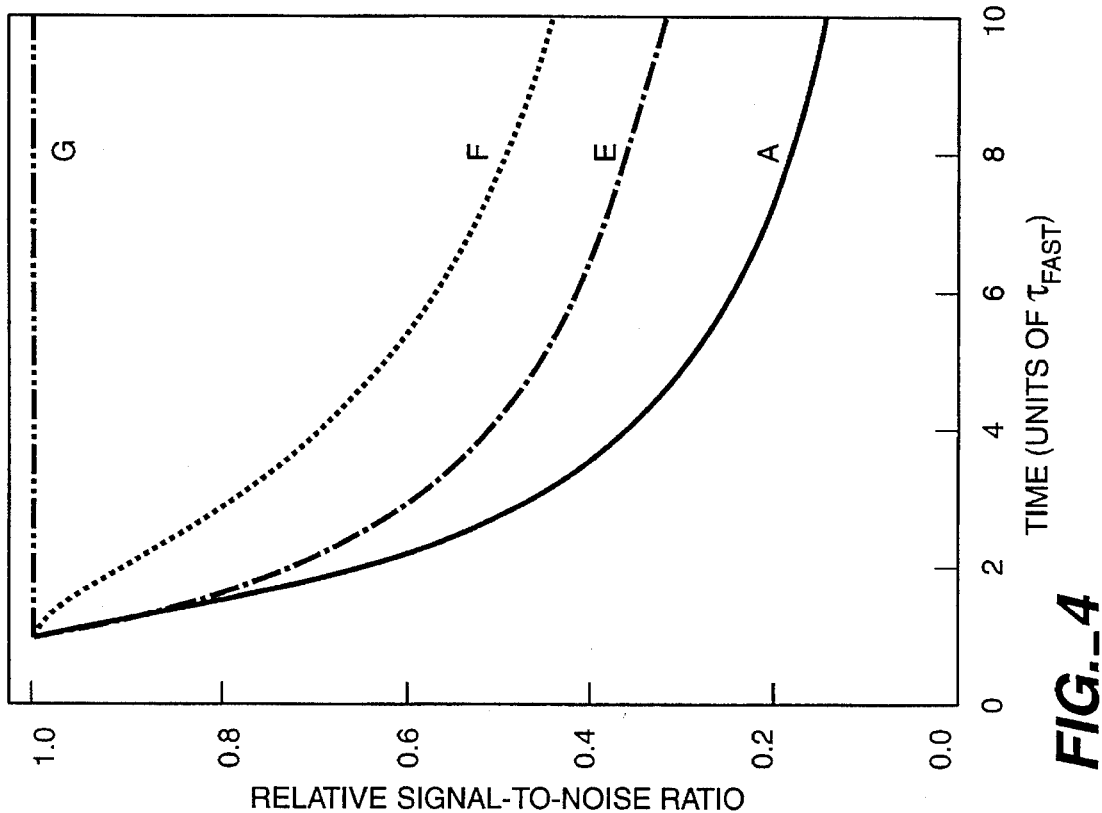
FIG._4
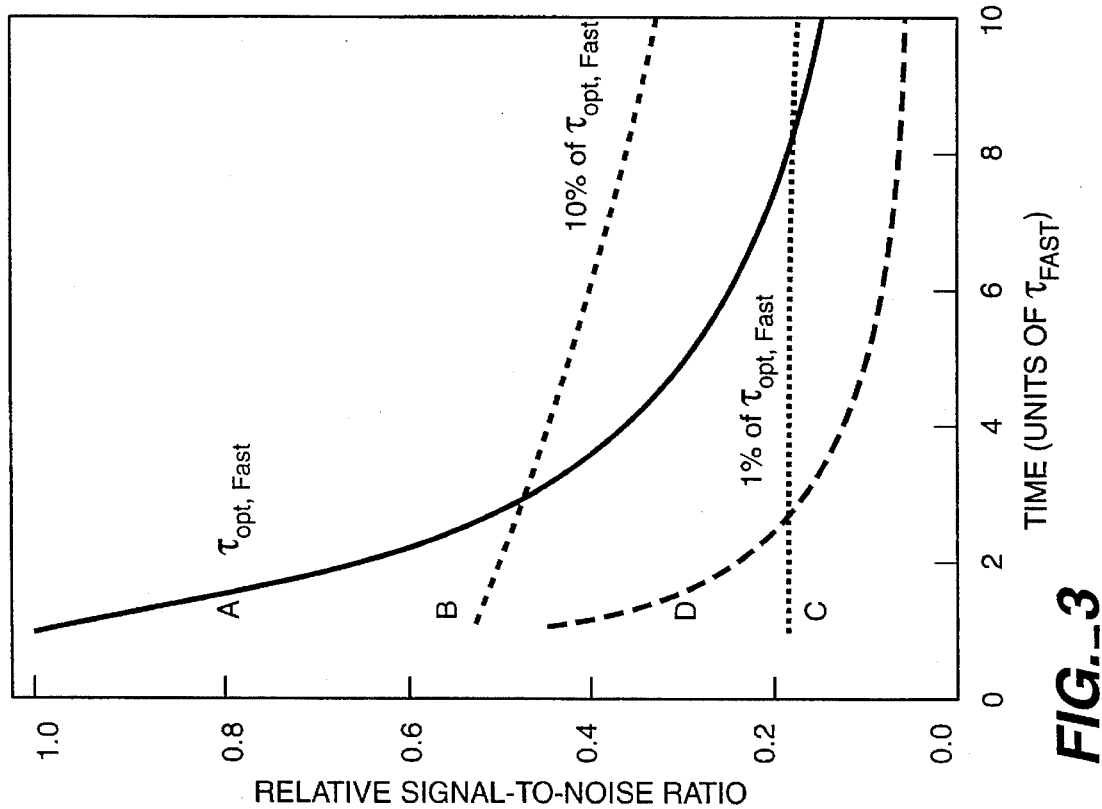
FIG._3

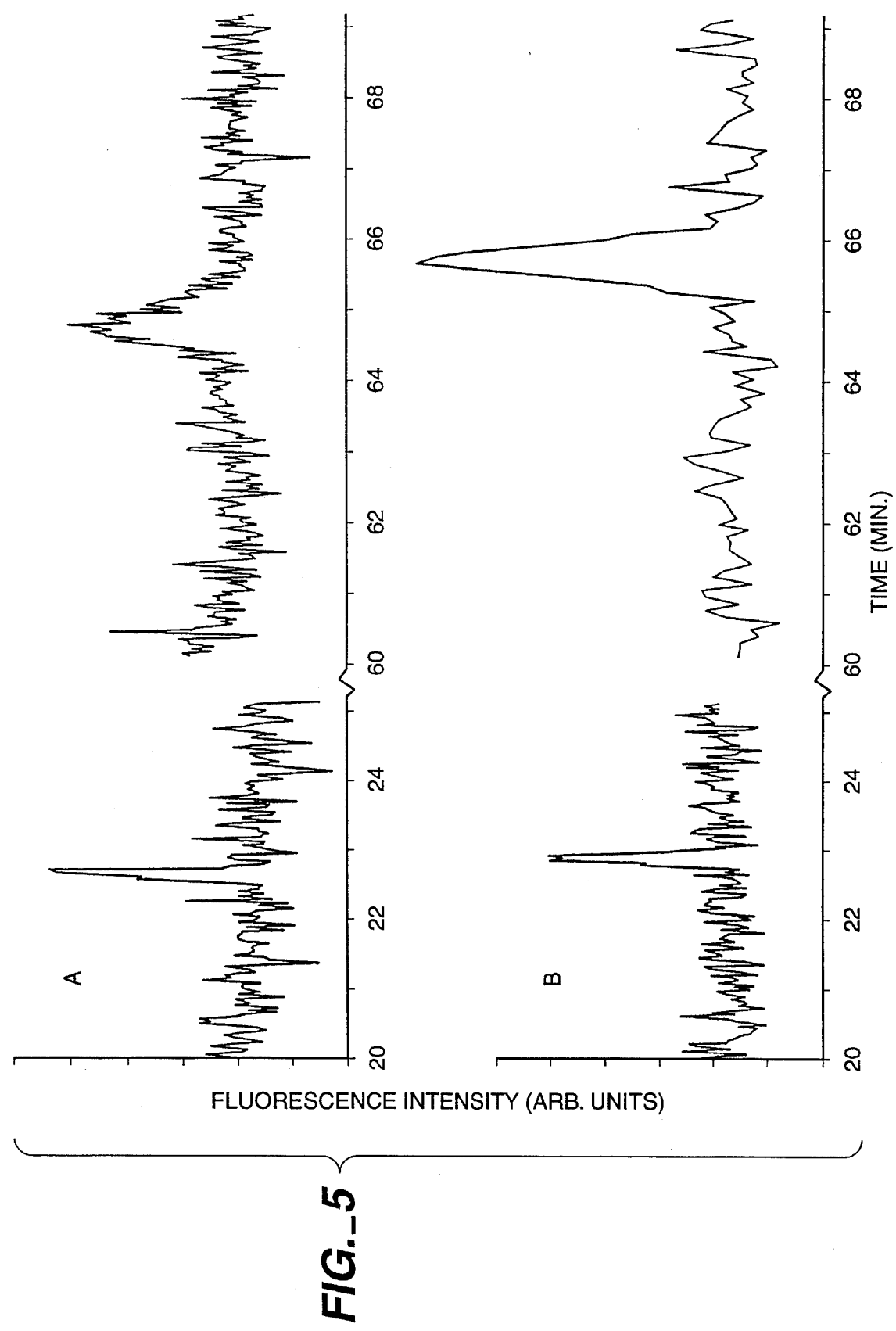
FIG._5

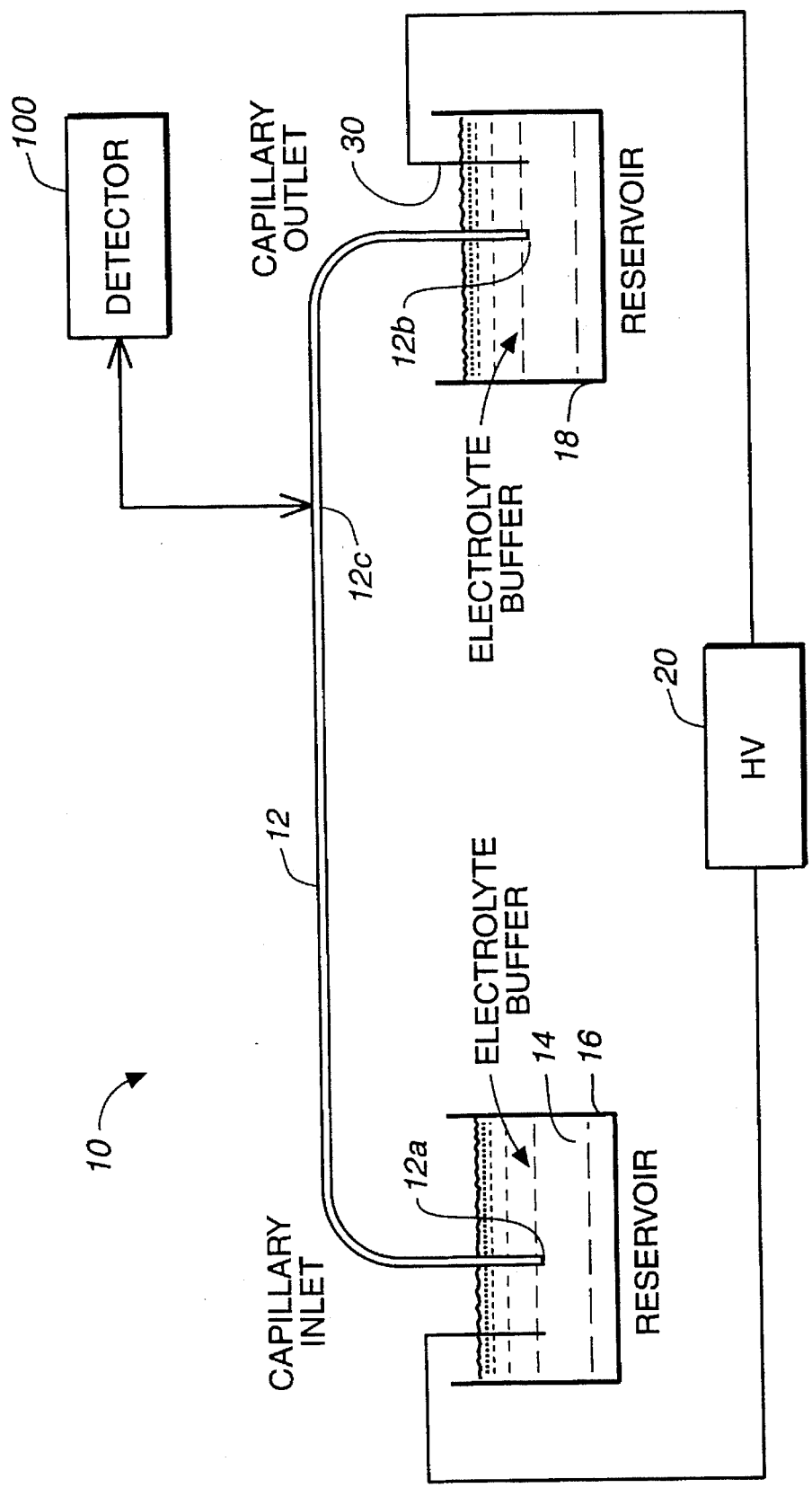
FIG._6

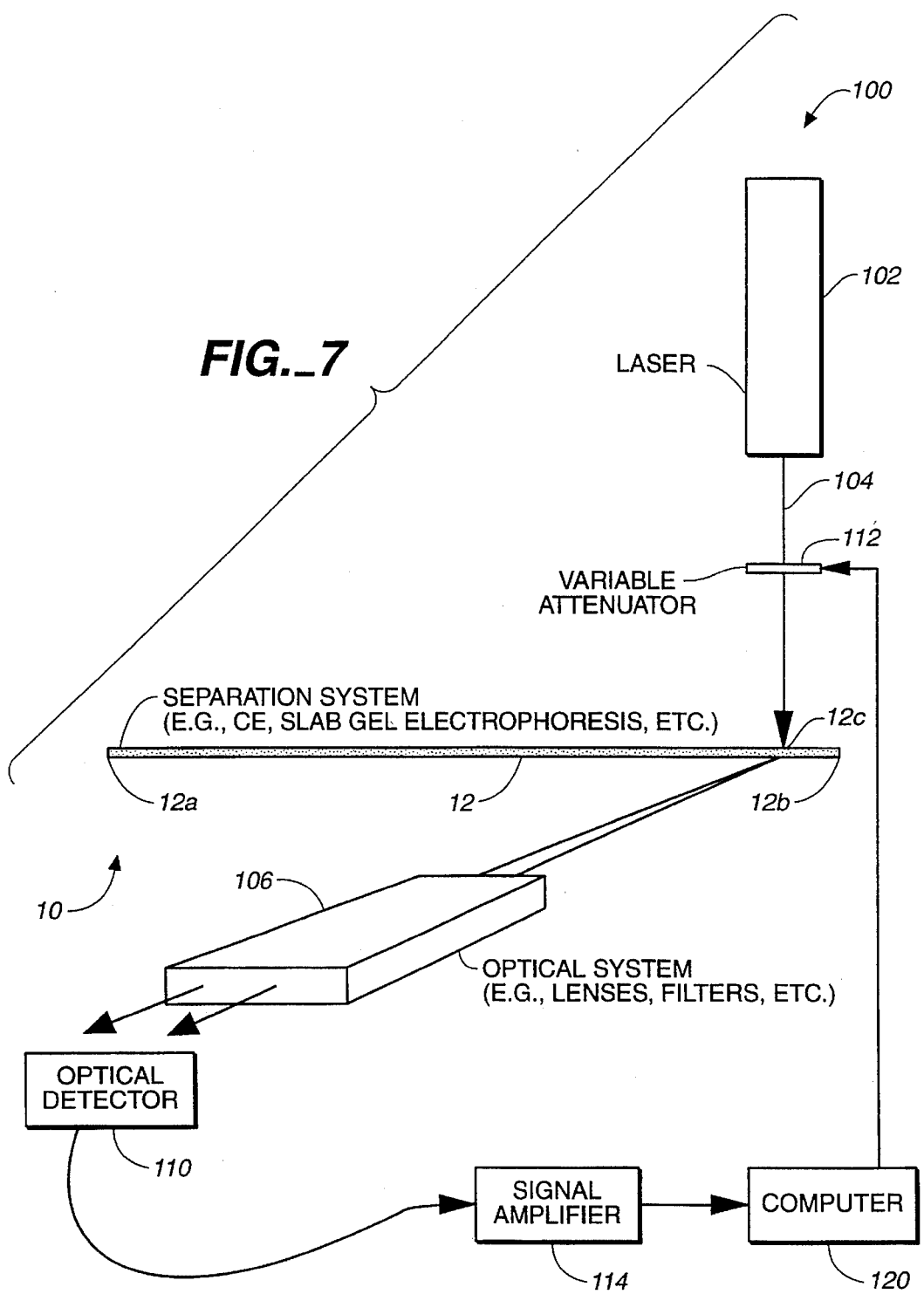
FIG._7

SYSTEM FOR SAMPLE DETECTION WITH COMPENSATION FOR DIFFERENCE IN SENSITIVITY TO DETECTION OF COMPONENTS MOVING AT DIFFERENT VELOCITIES

This invention was made with support from the United States Government under Grant No. NIH5R01MH45423-03. The Government has rights in this invention.

BACKGROUND OF THE INVENTION

This invention relates in general to a system for detection of sample components and in particular to a system for detection of sample components where the difference in sensitivity to detection of the components moving at different velocities is compensated for.

Historically, most electrophoretic and chromatographic separation techniques have employed off-line detection systems. Detection in high performance liquid chromatography is typically performed in a post-column flow cell and in slab gel electrophoresis, measurement of bands is often accomplished by staining the gel after electrophoretic separation. Recently, a variety of separation techniques have taken advantage of on-line detection to simplify analysis and improve reliability. As described in L. M. Smith, et al., *Nature*, 321:674–679 (1986), Smith et al. developed a fluorescence system for on-line detection with a polyacrylamide tube gel that measured DNA bands as they migrated past the focus of a laser beam. This procedure eliminated the need for manual analysis and the requirement for running multiple, overlapping gels. A similar approach that used 1 fluorescence detection for slab gel electrophoresis has been described by Middendorf et al. See, for example, L. R. Middendorf, et al., *Electrophoresis*, 13:487–494 (1992). Microcolumn procedures capable of separating low volume samples have employed on-line detection almost exclusively because of the ease of implementation — the separation channel is often made of fused silica and is therefore optically transparent — and the relative difficulty of making off-column plumbing connections with low-volume channels.

In addition to fluorescence detection, other detection methods have also been used in electrophoretic and chromatographic separation techniques, such as absorbance, electrochemical, chemiluminescence, radioisotope and four-wave mixing. In most of the above-mentioned detection methods, including fluorescence detection, the situation often arises where the detection sensitivity is limited by shot noise, which follows Poissons statistics. In such cases, it is useful for all analytes to be detected in an unbiased manner so that the detection signal can be faithfully related to the concentration of the analyte band in the detection zone. This goal is not achieved in traditional on-line detection techniques because of difficulties which may be inherent in the detection process.

In fluorescence detection, for example, quantitation often has involved labeling the analytes of interest with the same fluorescent tag and treating the fluorescent signal as proportional only to the fluorescence quantum yield and absorption cross-section of the tag and the concentration of the analyte. Frequently, a fluorescently-tagged standard having a known concentration is added to the sample mixture. A laser is then directed to the migrating sample components as they pass a detection zone to excite the components into light emission. The laser, however, also photobleaches portions of the components, thereby rendering such portions permanently undetectable. The detection process can destroy the detectable qualities in a number of other detection techniques other than fluorescence detection, such as in absorbance, electrochemical, chemiluminescence and four-wave mixing detection. In on-line detection systems, different components pass the zone at different velocities, and a greater fraction of the slower moving components may be photobleached than the faster components so that slower components exhibit smaller peaks if the detection is optimized for the faster components. In conventional on-line detection techniques, such effects are ignored, and the size of the corresponding peak is referenced to determine the concentration of a known species. Such approach does not take into account the effects of band velocities on detection sensitivity or the fact that the process of detection itself may destroy the detectability of fractions of the analyte band.

From the above, the traditional detection approach not only causes inaccuracies in quantitation, but may fail to detect a component altogether. Where the amount of a sample component is small so that it is barely detectable at optimum detection conditions, such component will become undetectable if detection conditions are optimized for a component different from such component as would be the case in traditional on-line detection. It is therefore desirable to provide an improved detection system for use in sample separation in which the above-described difficulties are alleviated.

SUMMARY OF THE INVENTION

This invention is a solution to the above problems based on the recognition that in many detection techniques, fractions of the sample components are rendered undetectable by the detection process. If all the sample components are travelling at the same speed through the detection zone, the fact that fractions of different components are destroyed will not affect the relative amplitudes of the peaks of the different components detected. However, if the different components travel through the detection zone at different speeds, the slower components will spend a relatively longer time in the detection zone compared to faster components so that a greater fraction of the slower components will be rendered undetectable compared to that of faster components. This will therefore reduce the relative amplitude of the detection signal for slower components compared to that for the faster components because less signal is generated per data point. By compensating for the difference in sensitivity to detection of components moving at different velocities, this invention reduces the disparity described above.

One aspect of the invention is directed towards a method for separation and detection of components of a sample. The method comprises the steps of causing components of the sample to migrate at different velocities along a direction and separate, and detecting the components when they are migrating at different velocities. Fractions of the components are altered by the detecting step so as to become undetectable. Unless compensated for, the components migrating at different velocities have different sensitivity to the detecting step. The detecting step is such that it is alterable by altering detection parameters. The detecting step is also such that one or more detection parameters is altered to compensate for the difference in sensitivity to detection of components moving at different velocities. Such alteration does not significantly affect the velocities of the components.

Another aspect of the invention is directed towards an apparatus for separation and detection of components of a sample. The apparatus comprises a first device causing components of the sample to migrate at different velocities along a direction and separate, and a second detecting device detecting the components when they are migrating at different velocities. Fractions of the components are altered by the detection so as to become undetectable. Unless compensated for, the components migrating at different velocities have different sensitivity to the detection. The detecting device has alterable detection parameters. The detecting device is such that one or more parameters is alterable to compensate for the difference in sensitivity to detection by the components moving at different velocities, without significantly affecting the velocities of the components.

Yet another aspect of the invention is directed towards a method for detection of components of a sample migrating at different velocities along a direction. The method comprises the steps of placing a detector having alterable detection parameters in spatial relation with the components, and detecting the components when they are migrating at different velocities by means of the detector. Fractions of the components are altered by the detecting step so as to become undetectable. Unless compensated for, the components migrating at different velocities have different sensitivity to the detecting step. The detecting step is such that one or more detection parameters is altered to compensate for the difference in sensitivity to the detection of components moving at different velocities. The alteration does not significantly affect the velocities of the components.

Still another aspect of the invention is directed towards an apparatus for detection of components of a sample migrating at different velocities along a direction. The apparatus comprises a first detection device detecting the components when they are migrating at different velocities, wherein fractions of said components are altered by the detection so as to become undetectable. Therefore, components migrating at different velocities have different sensitivity to the detection. The detecting device has alterable detection parameters. The apparatus further comprises a second device altering one or more detection parameters to compensate for the difference in sensitivity to detection of components moving at different velocities. Such alteration does not significantly affect the velocities of the components.

BRIEF DESCRIPTION OF THE DRAWINGS

FIGS. 1a, 1b are electropherograms illustrating a comparison of the signal-to-noise ratio for detection of fluorescein migrating at a faster and a slower velocity respectively before different velocity compensation procedures of this invention are implemented, under detection conditions optimized for the faster moving fluorescein.

FIG. 1c is an electropherogram illustrating a comparison of the signal-to-noise ratio for detection of fluorescein migrating at the same slower velocity as that illustrated in FIG. 1b, but different from FIG. 1b in that data-digitization rate has been reduced has been re-optimized for the slower velocity.

FIG. 1d is an electropherogram illustrating a comparison of the signal-to-noise ratio for detection of fluorescein migrating at the same slower velocity as that illustrated in FIG. 1b, but different from FIG. 1b in that both the excitation intensity and data-digitization rate has been reduced have been re-optimized for the slower velocity to remaximize the signal-to-noise ratio.

FIG. 2 is a graphical illustration of the calculated signal-to-noise ratio as explained in the Appendix.

FIG. 3 is a graphical plot relating the calculated fluorescence signal-to-noise ratio in CE separations for bands arriving at the detection zone over a 10-fold range in separation times using a 1,000-fold range in excitation intensities. The data-digitization rate is held constant, and is set to a value that generates 10 data points for the earliest detected band. Curves A, B, C and D demonstrate the effects of using an excitation intensity that is a multiple of 1, 0.1, 0.01, and 10 times the optimal intensity, respectively, for the earliest detected band.

FIG. 4 is a graphical plot of the calculated fluorescence signal-to-noise ratio as a function of migration time in CE separations in which the detection system is compensated for analyte velocity through different procedures. In all of the plots, excitation intensity is initially optimized for the earliest detected band detected at $\tau_{fast}$, and a data-digitization rate is chosen so that the earliest detected band generates 10 data points. Curve A is the result of employing no compensation. Curve E is produced by attenuating the excitation intensity by a factor of the ratio of the migration time of the earliest detected band to the migration time. Curve F is produced by attenuating the data-digitization rate by the same factor, and curve G is produced by attenuating both the excitation intensity and the data-digitization rate by such factor. Note the uniformity of the sensitivity at all time points in curve G.

FIG. 5a is a graphical plot of the fluorescence intensity as a function of migration time of the separation of fluorescein-arginine and fluorescein-glutamate before the application of the velocity compensation procedures of this invention are implemented.

FIG. 5b is a graphical plot of fluorescence intensity verses time for the same separation as in FIG. 5a, except that both the excitation intensity and the data-digitization rate have been attenuated by the ratio of the velocity of the fluorescein-glutamate band to the velocity of the fluorescein-arginine band after the detection of the fluorescein-arginine.

FIG. 6 is a schematic diagram of a CE system useful for illustrating the invention.

FIG. 7 is a schematic view of the system of FIG. 6, where the detection system of FIG. 6 is illustrated in more detail.

For simplicity and description, identical components in different figures of this application are labeled by the same numerals.

DETAILED DESCRIPTION OF THE PREFERRED EMBODIMENT

Before describing the system of this invention for optimizing signal-to-noise ratio (S/N or SNR), it is useful to first consider several related issues, the first being optimal laser intensity. To assess the sensitivity for fluorescence measurements in CE and other separation techniques, we assume that detection is performed during the separation process, so that an analyte band passes the detection zone at a velocity inversely proportional to the time elapsed since the separation was started. FIG. 3 demonstrates the calculated sensitivity during CE separations for excitation intensities that range 1,000-fold, with the excitation intensity and data digitization rate held constant throughout each separation. The data digitization rate is chosen so that a band arriving at the detection zone at the earliest time ($\tau_{fast}$) will generate 10 data points. Arrival time of a band at the detection site is plotted along the x axis. Curve A displays the result of employing an excitation intensity necessary for optimal sensitivity at time $\tau_{fast}$. We refer to this intensity as $I_{opt,fast}$. Curves B and C show the effect of operating at 10% and 1%, respectively, of $I_{opt,fast}$, while Curve D is the result of employing an excitation intensity that is a factor of ten greater than $I_{opt,fast}$. Intensities moderately lower than $I_{opt,fast}$ result in a less precipitous fall in the SNR and can yield better sensitivity late in a separation. Excitation intensities far below $I_{opt,fast}$ can be employed to obtain a nearly uniform response when absolute sensitivity is not a limiting factor. Because a very small fraction of analyte molecules is destroyed during transit through the detection zone under such conditions, even at relatively late time points, the measured fluorescence per molecule continues to increase with separation time at a rate sufficient to offset the loss in sensitivity that accompanies lower analyte flux through the detection zone. By using an intensity of 0.01 $I_{opt,fast}$, a nearly flat response is seen over a factor of 10 in migration times, although the sensitivity at time $\tau_{fast}$ is less than 20% of the maximal value. Finally, operating at an intensity greater than $I_{opt,fast}$ results in a relatively poor SNR at the outset that rapidly worsens as the separation proceeds. These results demonstrate that sensitivity cannot be improved without limit by increasing the excitation intensity in the detection zone; an optimum intensity exists for a given migration rate. Moreover, employing intensities lower than optimal is often better than using those higher than optimal. It is found that the optimum intensity results in about 70% photoalteration when measurements are limited by shot noise in the background.

In conventional fluorescence detection methods resulting in photoalteration of the detectable characteristics of samples, an optimum laser intensity is typically found by trial and error. We found that it is possible to set the laser intensity to a preset value without the conventional trial and error process as explained below.

FIG. 2 is a graphical plot of the calculated signal-to-noise ratio as explained in the Appendix. In FIG. 2, the maximum in the SNR represents the point at which the infinitesimal fractional change in fluorescence signal equals the infinitesimal fractional change in noise. Using the specified system parameters of FIG. 2, this maximum falls at $\delta t/6 \approx 0.45$ and $q \approx 6.3$, (q and $\delta t$ being defined in the Appendix) which respectively correspond to the summation of the fluorescence from approximately the centermost 80% of molecules in a band and an excitation intensity that results in approximately 70% photoalteration. Although the optimal value of q is dependent on photophysical characteristics, the optimal fraction of molecules that should be photoaltered during transit of the detection zone and the fraction that should be integrated within a single data point are independent of the photophysical parameters and the concentrations of the analytes.

Another related issue is data rate of detection. Two principal factors limit employment of the long integration windows that, in theory, yield the highest sensitivity measurements. First, there is some minimum acceptable number of data points that satisfactorily defines a peak. Second, our calculation for optimal sensitivity is based on an integration window centered at the midpoint of the band, and any large deviation from this condition results in significantly lower fluorescence signal. Generation of an intermediate number of data points per band (e.g., ~10) accurately defines most peaks, ensures that some data point will be centered closely about the true center of the band, and maintains a high SNR.

This invention is based on the observation that, by altering detection parameters such as the laser intensity and/or data rate of detection, it is possible to achieve the ideal SNR for separation of components with different mobility in the same process. Where fluorescence detection or other detection system is employed, uniform response is possible at all time points without sacrificing sensitivity. FIG. 4 is a plot of the SNR versus migration time $\tau$ and demonstrates the feasibility of this goal. As in FIG. 3, Curve A in FIG. 4 demonstrates the declining sensitivity experienced if excitation intensity and data digitization rate are optimized for a band that arrives at the detection zone at time $\tau_{fast}$ and are held constant. By attenuating excitation intensity throughout the separation by a factor of $\tau_{fast}/\tau$ to compensate for decreasing band velocities, an improvement in sensitivity at later times is achieved (see Curve E). In this case, the data digitization rate is still held constant during the separation. Curve F shows the effect of compensating the data digitization rate (without compensating the excitation intensity) so that all bands, regardless of residence time, generate the minimum acceptable number of data points. Compensation is accomplished by making the integration time for a data point proportional to elapsed time since the start of the separation. When both excitation intensity and the data digitization rate are adjusted during a separation to compensate for declining band velocities, uniform sensitivity with the highest possible SNR is achieved for each peak, regardless of migration velocity. This result is shown by Curve G. It is found that the alteration of the excitation intensity and data-digitization rate does not produce observable changes in the velocities of the sample components. Thus, such alteration of the excitation intensity and data-digitization rate does not significantly or substantially affect velocities of the sample components as known to those skilled in the art.

FIG. 6 is a schematic view of an electrophoretic system 10 to illustrate the invention. The system 10 includes a capillary tube 12 with two ends 12a, 12b. Ends 12a, 12b are dipped respectively in reservoirs 16, 18. A high voltage is applied by power source 20 across the two reservoirs 16, 18 to apply an electrical potential separation gradient across the two reservoirs. A sample is introduced into the tube 12 by dipping end 12a, for example, into a sample vial, which is raised above end 12b, or where a voltage is applied between the vial and reservoir 18, to inject a plug of sample into end 12a. End 12a is then again dipped in reservoir 16. Source 20 then applies an electrical potential separation gradient across the tube, causing the sample plug to migrate towards end 12b and to separate into its components. A detector system 100 is used to detect separated components in a detection zone 12c of the tube.

A laser-induced fluorescence detection system 100 for CE was constructed to test the effects of excitation power and data digitization rate on the fluorescence SNR in system 10 as shown in FIG. 7 to illustrate an embodiment of the invention. To simplify the diagram, only tube 12 of system 10 is shown in FIG. 7. The sample introduced into tube 12 as described above has been labeled with a fluorescent reagent tag in a manner known to those skilled in the art. The tag will cause the separated sample components to fluoresce in response to laser light of the appropriate wavelength. In system 100, the light from a laser such as an argon ion laser 102 (e.g. Model 2017, Spectra Physics, Mountain View, Calif.) is focused onto detection zone 12c of capillary channel 12 preferably using a lens (not shown) along path 104. An optional optical system 106 could include a parabolic mirror and a plano-convex lens then transmits the fluorescence signal from sample components in detection zone 12c of the capillary to the optical detector 110. The excitation zone 12c on the capillary could be placed at the focus of a 1-inch diameter parabolic mirror (not shown) of system 106, identical to that described by Pentoney et al.; S. L. Pentoney, et al., *Electrophoresis*, 13:467–474 (1992). System 106 may include a 2-inch diameter 150-mm f.l. plano-convex lens (not shown) that then focuses the collected fluorescence onto, for example, the photocathode of a photomultiplier tube (PMT, not shown) (Model R4632, Hammamatsu, Inc., San Jose, Calif.) in an optical detector 110.

The attenuation of the laser intensity applied by attenuator 112 could be controlled by computer 120. Samples may be introduced to a 90-cm separation capillary by placing the inlet 12a in a sample vial raised 5 cm above the capillary outlet for 15 s. The distance from the inlet 12a to the detection zone 12c may be 45 cm. In one test, fluorescent derivatives of two amino acids, arginine and glutamate, are prepared separately in a pH 9.2 borate buffer (50% dimethyl formamide) using 1 mM carboxyfluorescein succinimidyl ester (Molecular Probes, Inc., Eugene, Oreg.) and excess amino acid. Using these reaction conditions, the labeling reagent is completely consumed by reaction with arginine, although hydrolysis of the succinimidyl ester appears to compete effectively with the glutamate-succinimidyl ester reaction.

Results

FIGS. 1a, 1b are electropherograms illustrating a comparison of the SNR for detection of fluorescein migrating at two different velocities before different velocity compensation procedures of this invention are implemented. In a first set of experiments, we demonstrate the general validity of the invention by measuring the fluorescence SNR for a single compound, fluorescein, that traverses the detection zone at two velocities differing by a factor of four in magnitude. A photon counting detection system is employed in these experiments. In the first separation, shown in FIG. 1a, a plug of fluorescein is electrophoresed using a voltage of 9 kV in a 5 mM disodium phosphate buffer. Under these conditions, the time between the injection of fluorescein and its arrival at the detection zone is $\tau_{9kV} \approx 23.7$ min, which corresponds to a velocity of $V_{9kV} \approx 0$–0.32 mm/s. Here, excitation intensity is optimized to yield the highest possible SNR which is observed to result in approximately 70% photoalteration of fluorescein ($I_{opt,9kv} \approx 45$ mW). The data integration time is set to 2 s to produce approximately 12 points per peak. In other words, with the fluorescein migrating at 0.32 mm/s, excitation intensity is optimized for this migration rate and a data digitization rate is employed that generates approximately 12 points over the time needed for this band to completely pass through the detection zone.

In the separation shown in FIG. 1b, all conditions remain identical to those used for FIG. 1a, except that the separation voltage is reduced to 2.5 kV, which decreases the fluorescein velocity to 26% of its initial value ($v_{2.5kV} \approx 0.08$ mm/s). (Although the velocity for fluoroscein should ideally scale as the separation voltage, a number of voltage-dependent phenomena can upset this relationship.) Note the increase in temporal bandwidth because of slower migration through the detection zone. In one demonstration of the concept, to minimize differences in spatial bandwidth that may be induced by diffusion, a high field setting (200 V/cm) is utilized until the band nears the detection zone. The capillary voltage is then reduced to 2.5 kV for the remainder of the separation. From FIG. 1a to 1b, the SNR decreases by more than a factor of 2.5, which agrees well with theory set forth in the Appendix. Because of the slower rate of transit of this band, approximately 50 data points are generated for this peak. Note the decrease in the SNR when fluorescein migrates at this slower velocity.

FIG. 1c is an electropherogram illustrating a comparison of the signal-to-noise ratio for detection of fluorescein migrating at the same slower velocity as that illustrated in FIG. 1b, but different from FIG. 1b in that data-digitization rate has been reduced has been re-optimized for the slower velocity. FIG. 1d is an electropherogram illustrating a comparison of the signal-to-noise ratio for detection of fluorescein migrating at the same slower velocity as that illustrated in FIG. 1b, but different from FIG. 1b in that both the excitation intensity and data-digitization rate has been reduced have been re-optimized for the slower velocity to remaximize the signal-to-noise ratio.

Thus a comparison of FIGS. 1a, 1b on the one hand and FIGS. 1c, 1d on the other illustrates advantages of the invention. By scaling the data digitization rate by a factor of $V_{2.5kV}/V_{90kV}(=0.26)$ the loss in sensitivity can be partially reversed. This effect is shown in FIG. 1c. In other words, as shown in FIG. 1c, with fluorescein migrating at 0.08 mm/s with the same excitation intensity as in FIGS. 1a, 1b, but with a data digitization rate scaled by the ratio of the slow-to-fast band velocities (=0.08/0.32), the peak is once again composed of approximately 12 points. Complete recovery of the fluorescence SNR is achieved by scaling the data digitization rate and the excitation intensity in concert, which is demonstrated in FIG. 1d. To obtain the result in FIG. 1d, the excitation intensity is also reduced by a factor of $V_{2.5kV}/V_{9kV}(=0.26)$. Hence, with fluorescein migrating at 0.08 mm/s with both the excitation intensity and the data digitization rate scaled by 0.08/0.32, the band in FIG. 1d receives the same amount of radiant energy and generates the same number of data points as the band in FIG. 1a, and consequently, the SNR is remaximized.

The applicability of these concepts to measurements performed on different analyte species derivatized with the same fluorescent probe is shown in FIGS. 5a, 5b. For these measurements, an analog charge integrator is used. To enhance the differences in migration velocity of fluorescein-arginine and fluorescein-glutamate, we employ a 25mM borate buffer (pH 7.6) with 30% methanol content by volume. Excitation intensity is initially optimized for fluorescein-arginine migrating in a separation field of 200 V/cm ($I_{opt,arg} \approx 35$ mW), and the data integration period (2 s) is selected to yield approximately 10 points for this peak. FIG. 5a displays a separation of fluorescein derivatives of arginine ($4 \times 10^{-11}$ M) and glutamate ($4 \times 10^{-10}$ M) using these conditions. (The actual concentration of fluorescein-glutamate is significantly lower than this nominal value because of the poor efficiency of the glutamate labeling reaction.) Both species are present close to the detection limit (SNR≈2.5).

In a second separation of the labeled amino acids, shown in FIG. 5b, the excitation intensity and data digitization rate are scaled to the detection time of each band by decreasing both parameters by a factor of 2.8 (equal to ratio of the migration times of the bands) after the detection of fluorescein-arginine. These corrections yield an improvement of approximately a factor of 2 in the SNR for fluorescein-glutamate.

These results show that the fluorescence SNR for a band can be dramatically affected by the velocity at which it transits the detection zone. Thus, manipulation of excitation intensity and data digitization rate is desirable whenever detection is performed on-line, where analytes are still undergoing separation from one another. Such instances are not limited to capillary electrophoresis.

For instances in which all bands migrate at similar velocities, little variation will occur in the SNRs, and compensation for band velocity may be unnecessary. There are, however, numerous instances in which species migrate at significantly different rates and are measurable only by using optimized conditions. In such cases, compensation for differences in analyte velocity are essential in detection and quantitation.

The above-described procedure may be generally applicable to different separation techniques, such as slab gel electrophoresis, capillary gel electrophoresis, and chromatography as well as capillary zone electrophoresis. First, the intensity of the radiation supplied, such as laser light, is set to the optimal intensity for a particular sample component. In many separations, this may be the fastest moving component so that the intensity and data-digitization rate are set to be optimal for detecting the earliest arriving band. In other separations, however, it may be desirable to set the intensity which is optimal for a slower moving band instead. The band or component for which the excitation intensity and data rate are optimized is referred to below as the reference band or component.

In conventional separation techniques, the optimal intensity for a particular band is usually found by a trial and error process. According to the predicted results of the theory set forth in the Appendix, this trial and error process may be omitted if certain information concerning the particular component is known, such as its absorption cross-section $\sigma$ and its radiation-alteration quantum efficiency $\phi$. If these two quantities of the particular component are known, then the radiation intensity that is optimal for detecting such component is substantially "$\frac{5}{4}(1/\sigma^*\phi)$" if limited by shot noise in the background.

Where the fluorescence readings in the detection system 100 have been compensated for as described above, it is possible to detect the relative concentrations or the relative number of molecules in a given volume of different sample components; in such event, the ratio of the concentrations of two separate components is simply given by the ratio of the amplitudes of their fluorescence peaks. Hence if the concentration or the number of molecules in a given volume of one component is known, the concentration or the number of molecules in the same volume of another component may be found by measuring the ratio of the amplitudes of their fluorescence peaks.

The excitation intensity and data-digitization rate may be two of the detection parameters of the detection process which may be altered to compensate for the different velocities of the different components migrating past the detection zone that are being detected. Such detection parameters may then be altered to compensate for different velocities of the different sample components. Where the detection process includes supplying radiation to the sample and detecting the response of the sample components to the radiation supplied, the radiation intensity supplied may be adjusted as a function of the ratio of either the migration time or the velocity of another sample component to that of the reference sample component. If the reference component is also the fastest moving sample component, then the radiation intensity and a data-digitization rate may be reduced by a factor proportional to the ratio of the velocity of the slower moving components to that of the fastest moving reference component.

While in the process described above, the data-digitization rate is altered on-line, that is, when the sample components detected migrate through the detection zone under the influence of a separation gradient, it will be understood that the data-digitization rate may be altered subsequently after the sample components have migrated through the detection zone and the peaks corresponding thereto are already recorded. This may be accomplished in reference to FIG. 7 by means of computer 120 in a binning process, whereby different data points may be collapsed into fewer data points. Such process is known to those skilled in the art and will not be elaborated here. Such subsequent binning also assumes that sufficient data points have already been taken in the detection process so that it is possible to combine the data points into a smaller number of data points.

In the preferred embodiment described above, the laser intensity is altered by using an attenuator 112. Attenuator 112 applies a variable amount of attenuation as controlled by computer 120. Thus, computer 120 may simply be set to control attenuator 112 in order to apply an attenuation which increases as a function of time to achieve the above-described or other possible time varying alteration of the laser intensity. In the embodiment of FIG. 7, laser 102 may be one that supplies a constant intensity laser beam. Alternatively, it is possible to employ a laser which emits a light beam of controllable intensity in response to a control signal from computer 120; in such event, attenuator 112 will be unnecessary. However, since it is more difficult to control the light output of a laser than to control the attenuation of a constant intensity laser, the configuration shown in FIG. 7 is preferable. Instead of attenuating the light output of the laser, it is also possible to compensate for different component velocities by reducing the energy delivered to the zone 12c by reducing the cross-sectional dimensions of the laser beam without changing its intensity. The energy delivered to the zone 12c and the data digitization rate are detection parameters that can be altered to compensate for different component velocities.

In addition to using visible or invisible light as a part of the detection mechanism, other forms of energy may also be used to interrogate the detection zone. The above-described compensation scheme for different velocity sample components is also possible in detection methods other than fluorescence detection, including absorption, chemiluminescence, electrochemistry, and four-wave mixing. While the method for separation described above is an electrical potential gradient, the invention is equally applicable where other methods for effecting analyte migration is used, such as pressure in liquid chromatography. Such and all other possible methods and systems are within the scope of the invention.

While the invention has been described above by reference to various embodiments, it will be understood that various changes and modifications may be made without departing from the scope of the invention which is to be limited only by the appended claims. For example, even though the invention techniques are described to be useful for detection techniques in which the signal-to-noise ratio is limited by shot-noise, the techniques may also be applicable where the detection techniques are not so limited.

Attached hereto as an integral part of this application is an Appendix. The figures referred to in this Appendix are the same as FIGS. 1a, 1b through 5a, 5b discussed above. It will be noted that even though the five assumptions listed under the heading "Theory" in the Appendix are useful for a rigorous mathematical treatment of the basis for different velocity compensation schemes described herein, these assumptions do not limit the usefulness of the invention described herein to contexts where one or more of the assumptions do not entirely apply.

Appendix

A theory is presented for predicting signal-to-noise ratios (SNRs) for fluorescence detection of analyte bands that move at different velocities through a detection zone. Maximum SNRs are obtained by scaling the data-digitization rate and excitation intensity to the velocity of each band.

Historically, most electrophoretic and chromatographic separation techniques have employed off-line detection systems. Detection in high performance liquid chromatography is typically performed in a postcolumn flow cell and in slab gel electrophoresis, measurement of bands is often accomplished by staining the gel after electrophoretic separation. Recently, a variety of separation techniques have taken advantage of on-line detection to simplify analysis and improve reliability. Smith et al.[1] developed a fluorescence system for on-line detection with a polyacrylamide tube gel that measured DNA bands as they migrated past the focus of a laser beam. This procedure eliminated the need for manual analysis, and the requirement for running multiple, overlapping gels. A similar approach that used fluorescence detection for slab gel electrophoresis has been described by Middendoff et al.[2] Microcolumn procedures capable of separating low volume samples have employed on-line detection almost exclusively because of the ease of implementation — the separation channel is often made of fused silica and is therefore optically transparent — and the relative difficulty of making off-column plumbing connections with low-volume channels.

The advent of microcolumn separation techniques has placed great demands on detection systems. Because column diameters are typically 100 μm or less, UV absorption often yields inadequate detection limits. Among the various low-background techniques, laser-induced fluorescence detection has proved most sensitive; detection of fewer than 1000 analyte molecules, and at concentrations less than one picomolar, are possible for capillary electrophoresis (CE).[3,4] Despite these impressive developments, little consideration has been given to the effects of disparate band velocities on detection sensitivity. Huang et al.[5] noted that for on-line detection with CE, an analyte band passes the detection window at a velocity inversely proportional to the time it arrives after the start of separation, an effect that contributes to an increasing temporal width of peaks as separation time increases. The consequences of this broadening on radio-isotope detection have been discussed by Pentoney et al.[6]

Many factors must be considered in optimizing fluorescence detection systems. A stable excitation source and an efficient photodetector that contributes minimally to the overall noise are both critical. In addition, an optical system that maximizes light collection while discriminating analyte fluorescence from background is indispensible. Less obvious is the role played by excitation intensity. White and Stryer[7] presented theory addressing laser-induced photoalteration of dyes in flowing streams of different velocities. The prediction that excitation intensity must change proportionally to flow velocity to obtain equivalent photoalteration at all flow velocities was experimentally verified for several fluorescent species. Mathies et al.[8] later developed a more comprehensive treatment by considering the effects of both photoalteration and ground-state depletion on the optimization of excitation intensity and excitation time in flowing streams.

For separations in which analyte bands traverse the detection zone at different velocities, significant variability in the detection sensitivity can occur. This effect is shown in FIGS. 1a and 1b. Here, fluorescein is electrophoresed in a capillary at 2 different velocities: (1) a "rapid" velocity of 0.32 mm/s (FIG. 1a) and (2) a "slow" velocity of 0.08 mm/s (FIG. 1b). The excitation intensity is the same in both cases (but is optimized for the faster velocity) and the data-digitization rate is held constant. To explain the degradation in the signal-to-noise ratio (SNR) for the slower band, we expand upon the work of White and Stryer[7]. A theory is developed that relates the SNR of a fluorescence peak to excitation intensity and data-digitization rate under moderate intensity excitation conditions. This work shows that for a separation in which the excitation intensity and data-digitization rate have been optimized for a fast-traveling band, which arrives at the detection zone at a separation time of $\tau_{fast}$, the SNR can be maintained for all time points only if the radiant energy per band and the number of data points generated per peak are held constant. These conditions are met by continuous attenuation of the excitation intensity and of the digitization rate by a factor of $\tau_{fast}/\tau$, where x is the time elapsed since the start of the separation. Only when these two steps are taken together can the detection system exactly compensate for band velocity: all molecules are exposed to the same amount of radiant energy regardless of residence time in the detection zone, and all data points contain equivalent counts of background scatter and have a fluorescence signal proportional to analyte concentration.

Numerical analysis of the SNR reveals that compensation can prevent substantial losses in sensitivity as band velocity decreases. For the typical range of migration velocities in a CE separation, a nearly uniform SNR can be obtained without velocity compensation by using a lower than optimal excitation intensity. This approach, however, should be employed only when measurements are not hindered by inadequate sensitivity.

In the following sections we derive a general expression for the SNR of shot-noise-limited on-line fluorescence detection, and we compare theoretical predictions to experimental observations for CE.

Theory

The following assumptions are made:

1. Sensitivity is limited by shot noise in the background, which increases with the square root of the product of excitation intensity and the integration time of a data point.

2. The act of detection destroys some fraction of the analyte with first-order kinetics but does not alter whatever is responsible for the background noise.

3. All analyte species have identical photophysical characteristics (often a good approximation when analytes are tagged with the same fluorophore).

4. The proportion of molecules that occupy the triplet state is minimal, and excitation intensities are sufficiently low that the ground electronic state remains essentially fully populated.

5. All analyte bands are characterized by the same general shape.

The effect of detection on the measurable qualities of an analyte must be examined. Most chemical detection techniques are destructive to some degree. In fluorescence detection, electronic excitation of an analyte molecule can result in photoalteration (permanent photobleaching). Branching ratios of fluorescence to photoalteration (from the $S_1$ excited state) rarely exceed $10^{6.9}$

A. Low Photoalteration Regime

The degree of photoalteration during the passage of an analyte band through the detection zone dictates how much gain in integrated signal occurs when an analyte passes through the detection zone at a slower velocity. If, for example, fluorescence is measured from an analyte band traveling at a rapid velocity v, and the intensity of excitation results in photoalteration of only 1% of analyte molecules, the fluorescence signal for the entire band can be increased approximately two-fold by reducing the velocity to 0.5 v. Although the peak height will be nearly equivalent for the fast and slow band, the peak width will be greater for the slow band. Hence, the SNR for a data point integrated over the entire band will increase by approximately a factor of $\sqrt{2}$ in the shot noise limit. However, on-line detection typically does not integrate the signal from an entire analyte band. In nearly all cases a uniform data-digitization rate is employed; therefore, the number of data points produced per band scales inversely with the band velocity. The result of this procedure is that data points near the peak maximum of the slow band will have approximately the same SNR as do data points near the maximum of the fast band. (This conclusion is true only if the digitizing period is small in relation to the peak width.) Although an average of two times as much fluorescence is generated per analyte molecule in the slow band because of the increased residence time of a molecule in the detection zone, only half as many molecules pass through the detection zone during the integration period for a single data point for the slow band. Hence, in the limit of negligible analyte destruction, the fluorescence SNR remains constant, independent of analyte velocity.

B. High Photoalteration Regime

I. Measurements on stationary samples

When measurements are taken under conditions in which a large fraction of the molecules are destroyed, as would occur with more intense excitation or with very slow analyte bands, the SNR does not remain constant. For a stationary (nonmoving) sample in which ground-state depletion and triplet-state pileup are negligible and the noise in the background is much larger than the noise in the signal, the radiant energy required to achieve maximal fluorescence. sensitivity, $E_{opt}$, in a shot-noise-limited system is readily shown (see Appendix) to be:

$$E_{opt} \approx (5/4) \frac{1}{\sigma \phi_d} \text{ (photons cm}^{-2}) \quad (1)$$

where $\sigma$ is the absorption cross-section (cm$^2$ molecule$^{-1}$) and $\phi_d$ is the photoalteration quantum efficiency from the $S_1$ state. In this case, approximately 70% of the initial fluorescent molecules are photoaltered. Equation (1) demonstrates that for a single measurement taken on a stationary sample, the highest sensitivity can be obtained only when the sample is exposed to an optimum level of radiant energy.

II. Measurements on moving analyte bands

Fluorescence measurements performed during chemical separations require a more complex analysis. A moving analyte band that has a non-uniform concentration profile must be sampled multiple times as it crosses the detection zone to generate an accurate peak shape. The SNR for a data point is therefore a function of more than the laser intensity and the time of excitation; it is also dependent on the concentration profile of the band and the region of the band measured during the data point. In this treatment, analyte bands are assumed to conform to a gaussian distribution, although similar analyses could employ any well-defined peak shape. In addition, the spatial width of an analyte band is taken to be the length of the injection plug; that is, diffusion plays a minimal role in determining the band width. This is a useful assumption[10] and is often a reasonable approximation[6]; however, for instances in which diffusional broadening cannot be ignored, the present theory can be appropriately modified. We specify that an analyte band in a separation contains a total of $N_o$ molecules. The number of molecules per unit length at distance x from the start of the detection zone at time t is $$N_o(x,t) = \frac{N_o}{s_x (2\pi)^{1/2}} \exp\left( \frac{-[x - x_0(t)]^2}{2s_x^2} \right) \quad (2)$$

where $s_x^2$ is the spatial variance of the band and $x_o(t)$ is the position of the center of the band with respect to the beginning of the detection zone. Thus, in this equation, t=0 is defined as the time at which the peak maximum arrives at the start of the detection zone. We replace $x_o(t)$ by the product of velocity and t to obtain $$n_o(x,t) = \frac{N_o}{s_x (2\pi)^{1/2}} \exp\left( \frac{-(x - vt)^2}{2s_x^2} \right) \quad (3)$$

The detection zone length, L, is restricted to values much smaller than the band width (approximately $6s_x$), which is much smaller than the distance from the starting point of the separation to the detection zone.

We have ignored thus far the disappearance of fluorescing molecules caused by photoalteration. Photoalteration of fluorescent species is assumed to occur with first-order kinetics. Given our stated assumptions, the probability that a fluorescent molecule survives in a radiation field of intensity I (photons cm$^{-2}$ s$^{-1}$) to time t* can be approximated[8] by $$P(t^*) = \exp(-\sigma I \phi_d t^*) \quad (4)$$

The time a molecule has spent within the excitation zone, t*, can be related to the distance that the molecule has traveled across the excitation zone, x, and the band velocity, v, such that t*=x/v. (In most instances, the excitation zone is synonymous with the detection zone and will be taken as such in this treatment.) Hence, the distribution of photolabile fluorescing molecules in a moving gaussian band is $$n(x,t) = P(t^*) n_o(x,t) = \frac{N_o}{s_x (2\pi)^{1/2}} \exp\left( -\left[ \frac{(x - vt)^2}{2s_x^2} \right] - \sigma I \phi_d x/v \right) \quad (5)$$

The rate of fluorescence is given by the product of the fluorescence rate constant ($k_f$), the proportion of time a molecule spends in the excited state $S_1$, represented by $\{S_1\}$, and n(x,t):

$$\frac{df(x,t)}{dx\, dt} = k_f \{S_1\} n(x,t) = \phi_f \sigma I\, n(x,t) \quad (6)$$

where $\phi_f$ is the fluorescence quantum efficiency. Substitution of equation (5) into equation (6) yields $$\frac{df(x,t)}{dx\, dt} = \frac{\phi_f \sigma I N_o}{s_x (2\pi)^{1/2}} \exp\left( -\left[ \frac{(x - vt)^2}{2s_x^2} \right] - \sigma I \phi_d x/v \right) \quad (7)$$

The total measured fluorescence from the detection zone in the time window $\delta t$ centered about time t is $$f = K_1 \frac{\Phi_f \sigma I N_o}{s_x (2\pi)^{1/2}} \int_0^L dx \int_{t-\delta t/2}^{t+\delta t/2} dt' \exp\left(-\left[\frac{(x-vt')^2}{2s_x^2}\right] - \sigma I \Phi_d x/v\right) \quad (8)$$

where $K_1$ is a constant that depends on the efficiency of fluorescence collection and the detector response. The excitation intensity, $I$, is related to the radiant energy, $Q$, by the square root of the band variance in time, $Q=Is_t=Is_x/v$. To aid in numerical integration, we define a dimensionless radiant energy parameter $$\tilde{q} = \sigma \phi_d Q \quad (9)$$

and we introduce the additional dimensionless parameters $\tilde{t}=t/S_t=tv/S_x$ and $\tilde{m}=x/S_x$. The detection time window therefore can be stated as a dimensionless parameter $$\delta \tilde{t} = \frac{\delta t}{s_t} \quad (10)$$

Because $\delta \tilde{t}$ represents the number of standard deviations of a gaussian band that passes through the detection zone within a single data point, the fraction of the total band width included in a data point is given by approximately $\delta \tilde{t}/6$.

We turn our attention to noise. In Poisson statistics, noise ($\eta$) scales as the square root of the total number of independent events. Therefore, baseline shot noise increases as a function of total scattered photons according to $$\eta = K_2 (I\delta t)^{1/2} = K_2 (\tilde{q} \delta \tilde{t}/\sigma \phi_d)^{1/2} \quad (11)$$

where $K_2$ is a constant that depends on the intensity of background, the collection efficiency of background, and the detector response.

We can now write a single expression for the fluorescence SNR of a data point taken over any window $\delta \tilde{t}$:

$$\frac{f}{\eta} = [KN_o \Phi_f (\sigma/\Phi_d)^{1/2}] (\tilde{q}/\delta \tilde{t})^{1/2} \int_0^{\tilde{m}} d\tilde{m}' \int_{\tilde{t}-\delta \tilde{t}/2}^{\tilde{t}+\delta \tilde{t}/2} d\tilde{t}' \exp\left(-\left[\frac{(\tilde{m}-\tilde{t}')^2}{2}\right] - \tilde{q}\tilde{m}'\right) \quad (12)$$

where $K=(2\pi)^{-1/2}(K_1/K_2)$. Note that the excitation intensity and the integration window appear only in the dimensionless parameters $\tilde{q}$ and $\delta \tilde{t}$, respectively. An immediate conclusion that can be drawn from equation (12) is that, given constant values for $\tilde{q}$, $\delta \tilde{t}$, and $\tilde{m}$, the ratio of the number of fluorescent molecules in two bands is given by the ratio of the heights of the peaks:

$$\frac{(N_o)_i}{(N_o)_j} = \frac{f_i}{f_j} \quad (13)$$

In many instances, nonfluorescent analytes are labeled with a highly fluorescent probe molecule prior to detection. In such instances, the right hand side of equation (12) must be multiplied by a scaling parameter. In the case of analytes with one potential labeling site this parameter can range in value from zero to one and represents the fraction of analyte molecules that reacts with the fluorescent probe. For analytes that have multiple reactive sites, this parameter can be greater than one, but does not necessarily scale with the number of tags per molecule because of fluorescence quenching effects.

Calculation of Signal-to-Noise Ratios

We employ standard numerical techniques to determine the relationship between $\tilde{q}$, $\delta \tilde{t}$, and the fluorescence SNR from equation (12). The result is depicted in FIG. 2. Here, we assume that a data point is integrated over the window $\delta \tilde{t}$, which is centered about $\tilde{t}=0$ (the point at which the center of the gaussian arrives at the detection zone). The detection zone has a scaled "length", $\tilde{m}=0.2$, which corresponds to an excitation spot of 50 μm with a band length of 1.5 mm ($6s_x$).

The maximum in the SNR represents the point at which the infinitessimal fractional change in fluorescence signal equals the infinitesimal fractional change in noise. Using the specified system parameters, this maximum falls at $\delta \tilde{t}/6 \approx 0.45$ and $\tilde{q} \approx 6.3$, which respectively correspond to the summation of the fluorescence from the centermost 80% of molecules in a band and an excitation intensity that results in 70% photoalteration. Although the optimal value of $\tilde{q}$ is dependent on photophysical characteristics, the optimal fraction of molecules that should be photoaltered during transit of the detection zone and the fraction that should be integrated within a single data point are independent of the photophysical parameters and the concentrations of the analytes.

Two principal factors limit employment of the long integration windows that, in theory, yield the highest sensitivity measurements. First, there is some minimum acceptable number of data points that satisfactorily defines a peak. Second, our calculation for optimal sensitivity is based on an integration window centered at the midpoint of the band, and any large deviation from this condition results in significantly lower fluorescence signal. Generation of an intermediate number of data points per band (e.g., ~10) accurately defines most peaks, ensures that some data point will be centered closely about the true center of the band, and maintains a high SNR.

To assess the theoretical sensitivity for fluorescence measurements in CE, we assume that detection is performed during the separation process, so that an analyte band passes the detection zone at a velocity inversely proportional to the time elapsed since the separation was started. FIG. 3 demonstrates the calculated sensitivity during CE separations for excitation intensities that range 1000-fold, with the excitation intensity and data-digitization rate held constant throughout each separation. The data-digitization rate is chosen so that a band arriving at the detection zone at the earliest time ($\tau_{fast}$) will generate 10 data points. Arrival time of a band at the detection site is plotted along the x axis. Curve A displays the result of employing an excitation intensity necessary for optimal sensitivity at time $\tau_{fast}$. We refer to this intensity as $I_{opt,fast}$. Curves B and C show the effect of operating at 10% and 1%, respectively, of $I_{opt,fast}$, while Curve D is the result of employing an excitation intensity that is a factor of ten greater than $I_{opt,fast}$. Intensities moderately lower than $I_{opt,fast}$ result in a less precipitous fall in the SNR and can yield better sensitivity late in a separation. Excitation intensities far below $I_{opt,fast}$ can be employed to obtain a nearly uniform response when absolute sensitivity is not a limiting factor. Because a very small fraction of analyte molecules is destroyed during transit through the detection zone under such conditions, even at relatively late time points, the measured fluorescence per molecule continues to increase with separation time at a rate sufficient to offset the loss in sensitivity that accompanies lower analyte flux through the detection zone. By using an intensity of 0.01 $I_{opt,fast}$, a nearly flat response is seen over a factor of 10 in migration times, although the sensitivity at time $\tau_{fast}$ is less than 20% of the maximal value. Finally, operating at an intensity greater than $I_{opt,fast}$ results in a relatively poor SNR at the outset that rapidly worsens as the separation proceeds. These results demonstrate that sensitivity cannot be improved without limit by increasing the excitation intensity in the the detection zone; an optimum intensity exists for a given migration rate. Moreover, employing intensities lower than optimal is often better than using those higher than optimal.

Ideally, a fluorescence-detection system should offer uniform response at all time points without sacrificing sensitivity. FIG. 4 demonstrates the feasibility of this goal. As in FIG. 3, Curve A demonstrates the declining sensitivity experienced if excitation intensity and data-digitization rate are optimized for a band that arrives at the detection zone at time $\tau_{fast}$ and are held constant. By attenuating excitation intensity throughout the separation by a factor of $\tau_{fast}/\tau$ to compensate for decreasing band velocities, an improvement in sensitivity at later times is achieved (see Curve E). In this case, the data-digitization rate is still held constant during the separation. Curve F shows the effect of compensating the data-digitization rate (without compensating the excitation intensity) so that all bands, regardless of residence time, generate the minimum acceptable number of data points. Compensation is accomplished by making the integration time for a data point proportional to elapsed time since the start of the separation. When both excitation intensity and the data-digitization rate are adjusted during a separation to compensate for declining band velocities, uniform sensitivity with the highest possible SNR is achieved for each peak, regardless of migration velocity. This result is shown by Curve G.

Experimental Section

A laser-induced fluorescence detection system for CE was constructed to test the effects of excitation power and data-digitization rate on the fluorescence SNR. In this system, the 488-nm excitation line from an argon ion laser (Model 2017, Spectra Physics, Mountain View, Calif.) is focused onto a 100-μm i.d. capillary channel (375 μm o.d.) using a 50-mm focal length (f.l.) lens. The excitation zone on the capillary is placed at the focus of a 1-inch diameter parabolic mirror, identicle to that described by Pentoney et at.[11] A 2-inch diameter 150-mm f.l. plano-convex lens then focuses the collected fluorescence onto the photocathode of a photomultiplier tube (PMT) (Model R4632, Hammamatsu, Inc., San Jose, Calif.).

To minimize collection of background, two or more 10-nm bandpass interference filters (maximum transmittance ≈ 60% between 545 nm and 550 nm) are positioned immediately in front of the collection lens. Baseline noise scales approximately with the square root of excitation intensity for the range of intensifies employed in the experiments.

Typically, the laser is operated at an output of 100–200 mW, and is attenuated prior to the capillary with a linear-graded neutral density filter (Melles Griot, Inc., Irvine, Calif.). The filter is mounted on a high-resolution translation stage to allow precise selection of the desired excitation intensity, and the intensity of the transmitted beam is measured using a power meter. The PMT is supplied with an operating voltage of 500 V when being used in a photon-counting mode and with a voltage of 600 V when being used for analog measurements.

Two different data collection systems are employed. The first system is a photon counting system (EG&G Princeton Applied Research, Princeton, N.J.) that can integrate the PMT current over specified time windows. Because the degree of scatter in our system is relatively high, a series of four bandpass filters is placed before the 2-inch lens to reduce the collection of background to levels compatible with photon counting. In the second data system, the PMT current is sent to an analog charge integrator (Acton Research Corp., Acton, Mass.) that is programmed from a computer to bin signal over a specified time window and to relay the measurement to the computer. Because the requirement for low background is not as stringent in this case as it is with photon counting, only two bandpass filters are employed.

For all experiments, samples are introduced to a 90-cm separation capillary by placing the inlet in a sample vial raised 5 cm above the capillary outlet for 15 s. The distance from the inlet to the detection zone is 45 cm. Fluorescent derivatives of two amino acids, arginine and glutamate, are prepared separately in a pH 9.2 borate buffer (50% dimethyl formamide) using 1 mM carboxyfluorescein succinimidyl ester (Molecular Probes, Inc., Eugene, Oreg.) and excess amino acid. Using these reaction conditions, the labeling reagent is completely consumed by reaction with arginine, although hydrolysis of the succinimidyl ester appears to compete effectively with the glutamate-succinimidyl ester reaction.

Results

In the first set of experiments we demonstrate the general validity of the theory by measuring the fluorescence SNR for a single compound, fluorescein, that traverses the detection zone at two velocities differing by a factor of four in magnitude. The photon counting system is employed in these experiments. In the first separation, shown in FIG. 1a, a plug of fluorescein is electrophoresed using a voltage of 9 kV in a 5 mM disodium phosphate buffer. Under these conditions, the time between the injection of fluorescein and its arrival at the detection zone is $\tau_{9kV} \approx 23.7$ min,. which corresponds to a velocity of $V_{9kV} \approx 0.32$ mm/s. Here, excitation intensity is optimized to yield the highest possible SNR which is observed to result in approximately 70% photoalteration of fluorescein ($I_{opt,9kV} \approx 45$ mW). The data integration time is set to 2 s to produce approximately 12 points per peak. In the separation shown in FIG. 1b, all conditions remain identical to those used for FIG. 1a, except that the separation voltage is reduced to 2.5 kV, which decreases the fluorescein velocity to 26% of its initial value ($v_{2.5kV} \approx 0.08$ mm/s). (Although the velocity for fluorescein should ideally scale as the separation voltage, a number of voltage-dependent phenomena can upset this relationship.) Note the increase in temporal band width because of slower migration through the detection zone. To minimize differences in spatial band width that may be induced by diffusion, a high field setting (200 V/cm) is utilized until the band nears the detection zone. The capillary voltage is then reduced to 2.5 kV for the remainder of the separation. From FIG. 1a to 1b, the SNR decreases by more than a factor of 2.5, which agrees well with theory.

By scaling the data-digitization rate by a factor of $V_{2.5kV}/V_{9kV}$ (=0.26) the loss in sensitivity can be partially reversed. This effect is shown in FIG. 1c. Complete recovery of the fluorescence SNR is achieved by scaling the data-digitization rate and the excitation intensity in concert, which is demonstrated in FIG. 1d.

The applicability of these concepts to measurements performed on different analyte species derivatized with the same fluorescent probe is shown in FIG. 5. For these measurements, the analog charge integrator is used. To enhance the differences in migration velocity of fluorescein-arginine and fluorescein-glutamate, we employ a 25 mM borate buffer (pH 7.6) with 30% methanol content by volume. Excitation intensity is initially optimized for fluorescein-arginine migrating in a separation field of 200 V/cm ($I_{opt,arg} \approx 35$ mW), and the data-integration period (2 s) is selected to yield approximately 10 points for this peak. FIG. 5a displays a separation of fluorescein derivatives of arginine ($4 \times 10^{-11}$ M) and glutamate ($4 \times 10^{-10}$ M) using these conditions. (The actual concentration of fluorescein-glutamate is significantly lower than this nominal value because of the poor efficiency of the glutamate labeling reaction.) Both species are present close to the detection limit (SNR $\approx 2.5$). In a second separation of the labeled amino acids, shown in FIG. 5b, the excitation intensity and data-digitization rate are scaled to the detection time of each band by decreasing both parameters by a factor of 2.8 after the detection of fluorescein-arginine. These corrections yield an improvement of approximately a factor of 2 in the SNR for fluorescein-glutamate.

Conclusion

These results show that the fluorescence SNR for a band can be dramatically affected by the velocity at which it transits the detection zone. Thus, continuous manipulation of excitation intensity and data-digitization rate should be considered whenever detection is performed on-line, where analytes are still undergoing separation from one another. Such instances are not limited to capillary electrophoresis.

For instances in which all bands migrate at similar velocities, little variation will occur in the SNRs, and compensation for band velocity may be unneccessary. There are, however, numerous instances in which species migrate at significantly different rates and are measurable only by using optimized conditions. In such cases, compensation for differences in analyte velocity are essential in detection and quantitation.

Begin by assuming that almost all molecules occupy the ground state $S_o$, that negligible triplet-state accumulation occurs, and that the noise in the background is much larger than the noise in the signal. To a good approximation, the rate equation for fluorescence then simplifies to $df/dt^* = \phi_f K_a N_o \exp(-k_a \phi_d t^*)$, which integrates to $$f(t^*) = \frac{\Phi_f}{\Phi_d} N_o [1 - \exp(-\sigma I \Phi_d t^*)]$$

Shot noise accumulates as $$\eta(t^*) = A(It^*)^{1/2}$$

where A is a constant that depends on the intensity of background, the collection efficiency of background, and the detector response.

If we let $(It^*)=E$, the total radiant energy in units of (photons cm$^{-2}$), and $\sigma \phi_d = \beta$, the signal to noise varies with E as $$\frac{f}{\eta}(E) = \frac{\Phi_f N_o}{\Phi_d A} [1 - \exp(-\beta E)] E^{-1/2}$$

The highest signal-to-noise ratio occurs when $d(f/\eta)/dE=0$. This equation can be solved using Newton's iterative method to yield the optimal radiant energy input:

$$= \frac{1.256}{\beta} \approx (5/4) \frac{1}{\sigma \Phi_d}$$

Substitution of $E_{opt}$ for $(It^*)$ in Equation (4) in the main text demonstrates that the maximum SNR is achieved when approximately 70% of the molecules are photoaltered.

Acknowledgments

We gratefully acknowledge the helpful advice and assistance of Neil Shafer. In addition, we thank Beckman Instruments, Inc., and the National Institute of Mental Health (Grant No. NIH5R01MH45423-03) for continued financial support. J.B.S. is a Howard Hughes Medical Institute Predoctoral Fellow.

References and Footnotes (1) Smith, L. M.; Sanders, J. Z.; Kaiser, R. J.; Hughes, P.; Dodd, C.; Connell, C. R.; Heiner, C.; Kent, S. B. H.; Hood, L. E. *Nature* 1986, 321, 674–79.

(2) Middendoff, L. R.; Bruce, J. C.; Bruce, R. C.; Eckles, R. D.; Grone, D. L.; Roemer, S.C.; Sloniker, G. D.; Steffens, D. L.; Sutter, S. L.; Brumbaugh, J. A.; Patonay, G. *Electrophoresis* 1992, 13, 487–94.

(3) Wu, S.; Dovichi, N.J. *Talanta* 1992, 39, 173–78.

(4) Fishman, H. A.; Shear, J. B.; Sweedler, J. V.; Zare, R. N. The Pittsburgh Conference on Analytical Chemistry and Applied Spectroscopy, Mar. 9–12, 1992, New Orleans, La.; oral presentation (Abstract 300).

(5) Huang, X; Coleman, W. F.; Zare, R. N.J. *Chromatogr.* 1989, 480, 95–110.

(6) Pentoney, S. L., Jr.; Zare, R. N.; Quint, J. F. J. *Chromatogr.* 1989, 480, 259–70.

(7) White, J. C.; Stryer, L. *Anal. Biochem.* 1987, 161, 442–52.

(8) Mathies, R. A.; Peck, K.; Stryer, L. *Anal. Chem.* 1990, 62, 1786–91.

(9) Soper, S. A.; Shera, E. B.; Martin, J. C.; Jett, J. H.; Hahn, J. H.; Nutter, H. L.; Keller, R. A. *Anal. Chem.* 1991, 63, 432–37.

(10) Inclusion of analyte diffusion coeffecients would expand FIG. 2 into 4-dimensional space (Calculation of Signal-to-Noise Ratios section), and would require that FIGS. 3 and 4 be depicted as 3-dimensional plots. Because band-broadening caused by diffusion is frequently a second-order effect (see reference (6)), consideration of analyte diffusion would unneccessarily complicate the presentation of the effects of the excitation intensity and data digitization on the SNR.

(11) Pentoney, S. L., Jr.; Konrad, K. D.; Wilbur, K. *Electrophoresis* 1992, 13, 467–74.

Experiments Illustrated in the Figures

FIG. 1. Comparison of the SNR for detection of fluorescein migrating at two different velocities before and after different velocity compensation procedures are implemented. (a) Fluorescein migrating at ~0.32 mm/s, using an excitation intensity optimized for this migration rate and employing a data-digitization rate that generates approximately 12 points over the time needed for this band to completely pass through the detection zone. (b) Fluorescein migrating at ~0.08 mm/s with the same excitation intensity and data-digitization rate as in (a). Because of the slower rate of transit of this band, approximately 50 points are generated for this peak. Note the decrease in the SNR when fluorescein migrates at this slower velocity. (c) Fluorescein migrating at ~0.08 mm/s with the same excitation intensity as in (a) and (b) but with a data-digitization rate scaled by the ratio of the slow-to-fast band velocities (=0.08/0.32) so that the peak is once again composed of approximately 12 points. (d) Huorescein migrating at ~0.08 mm/s with both the excitation intensity and the data-digitization rate scaled by 0.08/0.32. The band in (d) receives the same amount of radiant energy and generates the same number of data points as the band in (a), and consequently, the SNR is remaximized.

FIG. 2. Calculated three-dimensional surface plot relating the dimensionless parameters $\delta \tilde{t}$ and $\tilde{q}$ to the fluorescence SNR for a data point centered at the middle of the gaussian band. $\delta \tilde{t}/6$ is the fraction of the total band width integrated within the data point, $\tilde{q}$ is a parameter that scales linearly with the amount of radiant energy deposited per band, and $\tilde{q}_{opt}$ is the value of $\tilde{q}$ ($\approx 6.3$) when the SNR is optimized. Note that the maximum SNR occurs at $\delta \tilde{t}/6 \approx 0.45$ and $\tilde{q}/\tilde{q}_{opt}=1$.

FIG. 3. Plots relating the calculated fluorescence SNR in CE separations for bands arriving at the detection zone over a ten-fold range in separation times using a 1000-fold range in excitation intensities. A constant excitation intensity is employed for all points on the same curve. The data-digitization rate is held constant, and is set to a value that generates 10 data points for the earliest detected band (at time $\tau_{fast}$). Curves A, B, C, and D demonstrate the effects of using a excitation intensity that is 1x, 0.1x, 0.01x, and 10x the optimal intensity, respectively, for a band arriving at the detection zone at time $\tau_{fast}$.

FIG. 4. Plots relating the calculated fluorescence SNR in CE separations in which the detection system is compensated for analyte velocity through different procedures. Curve A is the result of employing no compensation, Curve E is produced by attenuating the excitation intensity by a factor of $\tau_{fast}/\tau$, Curve F is produced by attenuating the data-digitization rate by a factor of $\tau_{fast}/\tau$, and Curve G is produced by attenuating both the excitation intensity and the data-digitization rate by a factor of $\tau_{fast}/\tau$. In all cases, excitation intensity is initially optimized for time $\tau_{fast}$, and the data-digitization rate is chosen so that a band that arrives at the detection zone at time $\tau_{fast}$ generates 10 points.

FIG. 5. Separations of two fluorescein-labeled amino acids demonstrate the effect of velocity compensation on the SNR. (a) A separation of fluorescein,arginine ($\tau_{arg} \approx 22.6$ min.) and fluorescein-glutamate ($\tau_{glu} \approx 64.7$ min.) (concentrations are given in the text). Excitation intensity is optimized for the fast-migrating fluorescein-arginine and is kept constant throughout the separation. The data-digitization rate is chosen to generate approximately 10 points for the fluorescein-arginine peak and is also kept constant during the separation. Note that the glutamate peak is barely detectable. (b) A repeat of the separation in (a), except that the excitation intensity and the data-digitization rate are optimized for both peaks by attenuating these parameters by the ratio of the velocity of the fluorescein-glutamate band to the velocity of the fluorescein-arginine band following the detection of fluorescein-arginine. The fluorescein-glutamate peak is now easily detected.

What is claimed is:

1. A method for separation and detection of components of a sample, said method comprising the steps of:

causing components of the sample to migrate at different velocities and separate in a separation path;

supplying radiation to the components to cause the components to exhibit a detectable response, wherein fractions of said components are altered by the radiation so as to become undetectable;

detecting the response of the components when they are migrating at different velocities at a data rate;

wherein the intensity of the radiation supplied in the supplying step or the data rate of the detecting step is altered as a function of different lengths of migration time of the components to reduce differences in signal-to-noise ratio of components migrating at different velocities.

2. The method of claim 1, said supplying step further comprising the step of setting the intensity of radiation supplied to the sample to a predetermined value before radiation is supplied to the sample, wherein said intensity of radiation supplied is decreased from said predetermined value as a function of length of migration time.

3. The method of claim 2, wherein said detecting step includes setting the data rate of the response from the components of the sample to a second predetermined value for detecting a particular component of the sample, wherein said data rate is decreased from said predetermined value as a function of length of migration time.

4. The method of claim 2, wherein said setting step sets the intensity of radiation supplied to the sample to an optimum value for detecting a particular component of the sample, wherein the intensity of radiation is reduced to a value optimum for another component of the sample.

5. The method of claim 4, wherein said setting step sets the intensity of radiation supplied to the sample to an optimum value for detecting the fastest component of the sample, and wherein the intensity of radiation supplied is reduced from said optimum value as a function of length of migration time of said another component.

6. The method of claim 3, wherein said setting step sets the intensity of radiation supplied to the sample to substantially $(5/4)(1/\sigma^*\phi)$, where $\sigma$ is the absorption cross-section of the particular component, and $\phi$ is the radiation-alteration quantum efficiency of the particular component.

7. The method of claim 1, wherein said detecting step includes setting the data rate of the response from the components of the sample to an optimum value for detecting a particular component of the sample.

8. The method of claim 7, further comprising reducing the data rate during the migration and separation of the sample components and during the detecting step.

9. The method of claim 7, further comprising reducing the data rate after the detecting step.

10. The method of claim 1, said supplying step including providing a source of radiation of substantially constant intensity and attenuating the radiation from said source as a function of length of migration time of the components to reduce differences in signal-to-noise ratio of components migrating at different velocities.

11. The method of claim 1, further comprising altering the data rate of response detected after the detecting step.

12. The method of claim 1, wherein said components exhibit a response according to one of the following mechanisms in response to the radiation supplied:

fluorescence or absorption, and said detecting step detects the fluorescence or absorption response of the components.

13. The method of claim 1, further comprising labeling the sample with a fluorophore prior to the causing step.

14. The method of claim 1, said causing step including applying a separation gradient to the sample in a separation medium.

15. The method of claim 14, wherein said applying step applies an electrical potential gradient across the separation medium.

16. The method of claim 1, wherein said supplying step applies electromagnetic radiation to the sample.

17. A method for detection of components of a sample migrating at different velocities along a path, said method comprising the steps of:

supplying radiation to the components to cause the components to exhibit a detectable response, wherein fractions of said components are altered by the radiation so as to become undetectable;

detecting the response of the components when they are migrating at different velocities at a data rate;

wherein the intensity of the radiation supplied in the supplying step or the data rate of the detecting step is altered as a function of different lengths of migration time of the components to reduce differences in signal-to-noise ratio of components migrating at different velocities.

18. The method of claim 17, said supplying step further comprising setting the intensity of radiation supplied to the sample to a predetermined value before radiation is supplied to the sample, wherein said intensity of radiation supplied is decreased from said predetermined value as a function of length of migration time.

19. The method of claim 18, wherein said setting step sets the intensity of radiation supplied to the sample to an optimum value for detecting a particular component of the sample.

20. The method of claim 19, wherein said setting step sets the intensity of radiation supplied to the sample to an optimum value for detecting the fastest component of the sample, and wherein the intensity of radiation supplied is reduced from said predetermined value as a function of length of migration time.

21. The method of claim 19, wherein said setting step sets the intensity of radiation supplied to the sample to substantially $(5/4)(1/\sigma^*\phi)$, where $\sigma$ is the absorption cross-section of the particular component, and $\phi$ is the radiation-alteration quantum efficiency of the particular component.

22. The method of claim 17, wherein said detecting step includes setting the data rate of the response from the components of the sample to an optimum value for detecting a particular component of the sample.

23. The method of claim 22, wherein said setting step sets the data rate of the response from the components of the sample to an optimum value for detecting the fastest component of the sample, and wherein the data rate of detection of components of the sample is reduced from said predetermined value as a function of length of migration time.

24. The method of claim 23, wherein the data rate of detection of components of the sample is reduced during the detecting step.

25. The method of claim 23, wherein the data rate of detection of components of the sample is reduced after the detecting step.

26. The method of claim 17, said supplying step including providing a source of radiation of substantially constant intensity and attenuating the radiation from said source as a function of length of migration time of the components to reduce differences in signal-to-noise ratio of components migrating at different velocities.

27. The method of claim 17, further comprising altering the data rate of response detected after the detecting step.

28. The method of claim 17, wherein said components exhibit a response according to one of the following mechanisms in response to the radiation supplied: fluorescence or absorption, and said detecting step detects the fluorescence or absorption response of the components.

29. The method of claim 17, further comprising labeling the sample with a fluorophore prior to the supplying step.

30. The method of claim 17, wherein said supplying step applies electromagnetic radiation to the sample.

31. A method for detection of components of a sample migrating at different velocities along a path, said method comprising the steps of:

supplying radiation to the components in a detection zone of the path to cause the components to exhibit a detectable response, wherein fractions of said components are altered by the radiation so as to become undetectable;

detecting the response of the components when they are migrating in the zone at different velocities at a data rate;

wherein the intensity of the radiation supplied in the supplying step or the data rate of the detecting step is altered as a function of different lengths of migration time of the components in the zone to reduce differences in signal-to-noise ratio of components migrating at different velocities.

* * * * *